United States Patent [19]

Woodbury

[11] 4,134,067
[45] Jan. 9, 1979

[54] ROTARY EDDY CURRENT FLAW DETECTOR UTILIZING DIFFERENTIALLY UNBALANCED COILS AND THE AMPLITUDE OF A ROTARY INDUCED PULSE TO PRODUCE THE CHARGING VOLTAGE FOR THE SWEEP GENERATOR

[75] Inventor: Russell K. Woodbury, Renton, Wash.
[73] Assignee: The Boeing Company, Seattle, Wash.
[21] Appl. No.: 831,933
[22] Filed: Sep. 9, 1977
[51] Int. Cl.$^2$ .................. G01R 33/12; H03K 4/08
[52] U.S. Cl. ................................. 324/219; 324/241; 307/228; 328/185
[58] Field of Search .............. 324/219, 220, 221, 228, 324/233, 234, 236, 238, 237, 239, 240, 241, 242, 16 S; 328/185; 315/408, 410; 307/228

[56] References Cited

U.S. PATENT DOCUMENTS

| 2,604,515 | 7/1952 | McNulty | 324/16 S |
|---|---|---|---|
| 2,924,707 | 2/1960 | Chandler | 328/173 |
| 2,970,256 | 1/1961 | Sazynski et al. | 324/240 |
| 3,617,869 | 11/1971 | Germann et al. | 324/15 |
| 3,718,855 | 2/1973 | Rogel et al. | 324/202 |

FOREIGN PATENT DOCUMENTS

| 761594 | 6/1967 | Canada | 324/241 |
|---|---|---|---|
| 807487 | 6/1961 | United Kingdom | 324/237 |
| 907418 | 10/1962 | United Kingdom | 324/238 |

Primary Examiner—Robert J. Corcoran
Attorney, Agent, or Firm—Christensen, O'Connor, Johnson & Kindness

[57] ABSTRACT

A readily portable battery operated eddy current device is disclosed for detecting fissures, cracks or other defects in metal surfaces such as the walls of rivet holes in aircraft parts. Dual sensing transformer secondaries having a high-frequency energized common primary are embedded with pole faces peripherally exposed in a rotary detection probe insertable in a test hole. Differentially connected in a response circuit, these secondaries, constructed with slight mismatch between them, yield a composite response to the presence of a hole wall defect that when differentiated provides a uniquely definitive monopolar pulse of magnitude and relative phase position uniquely indicating on an oscilloscope screen the nature and the precise location of the defect. A stationary induction coil and a permanent magnet on the rotating probe produce cyclic pulses utilized to produce a cathode ray tube sweep that is both synchronized with probe rotation and that is maintained at substantially constant sweep magnitude despite variations in probe rotation speed and, for that matter, system operating voltage supplied by the battery.

6 Claims, 14 Drawing Figures

ROTARY EDDY CURRENT FLAW DETECTOR UTILIZING DIFFERENTIALLY UNBALANCED COILS AND THE AMPLITUDE OF A ROTARY INDUCED PULSE TO PRODUCE THE CHARGING VOLTAGE FOR THE SWEEP GENERATOR

BACKGROUND OF THE INVENTION

This invention relates to an improved eddy current rotary probe type testing device adapted for rapidly scanning the interior walls of tubes or holes in metal parts in order to detect faults such as fissures, cracks or other defects. A highly useful application is to inspect fastener holes in metal aircraft parts wherein strength or fatigue of structures are highly critical and the number of holes to be tested and their varying accessibility to apply the test, pose worker fatigue and performance problems. A broad object of this invention is to provide a compact, readily portable and consistently reliable test device of this nature suitable for such applications. More specifically it is an object for such purposes to provide an easily manipulated hand-held device that provides precise indications of fault location and magnitude even under varying operating conditions and when used by operators of limited skills and experience. The invention is herein illustratively described by reference to the presently preferred embodiment thereof; however, it will be recognized that certain modifications and changes with respect to details may be made without departing from the essential features involved.

While the principles of the invention may be applied to the detection of faults in surfaces other than the walls of fastener holes, this latter application is presently considered to be the most important and is therefore chosen as the basis for describing the invention.

A further object hereof is to provide such a test device that may be utilized rapidly and efficiently in testing a large number of holes over a relatively short time period and of doing so with a high degree of sensitivity and reliability of the indicated results.

A further advantage of this invention, which it shares with certain prior art rotary probe eddy current type testers, is that it incorporates sensing transformer elements in the probe differentially connected so as to cancel out and reject from the sensing circuit the effects of false responses due to transitional positioning of the probe, such as those that can occur when the probe is being inserted in and removed from a test hole. These transitional effects are sometimes designated by the characterizing terms "lift-off," "balance," or "directional edge" effects.

The present invention also utilizes differentially connected probe-mounted sensing transformer secondaries, but in this case they are deliberately slightly mismatched so as to provide a uniquely definitive output response. This invention also contemplates indication sweep circuit improvements of unique value to the bulk, weight and versatility requirements of the major objectives.

With battery power used to operate the circuits and also to drive the probe motor of the improved device, the unavoidable contacts of the rotating probe with the hole wall produce drag that can reduce the speed by a substantial percentage. Furthermore, battery voltage also drops with aging and prolonged usage. With these variable conditions in view, a further object hereof is to provide a fault detection indicator that depends in part for its consistency of results on an improved indicator sweep circuit operable independently of probe speed or, for that matter, battery voltage also. A number of prior art synchronized sweep circuits may be used in principle to provide sweep voltages of equal magnitude despite variable sweep recurrence frequency, examples include those discussed in the following designated U.S. Pat. Nos. 2,532,576; 3,002,153; 2,604,515; 3,292,092; 2,924,707; 3,323,353; 2,948,857; 3,577,007.

However, the present sweep system has specialized advantages, primarily in its low cost, compactness and reliable simplicity for broad purposes of the invention.

Still another object of this invention is to provide an improved fault detection system with complemental indicators, one a graphic display that delineates the specific character and location of the fault, and the other an alert display that prominently signals the presence of a fault so as to direct the operator's attention to the graphic display. As a result the operator need not strain in needless continuous concentration on the graphic (i.e., cathode ray tube) indicator over prolonged time periods while many holes are being successively tested. Furthermore, since the operator need not divert his attention from carefully positioning the test probe in successive test holes in order to study the relatively complex displays of the CRT indicator at every stage, the work becomes much less tiring and the results better on the average over the time of a work shift.

BRIEF DESCRIPTION OF THE INVENTION

In accordance with this invention, the improved eddy current rotary probe incorporates dual differentially connected eddy current reactive transformer secondaries that are slightly mismatched or unbalanced to a predetermined degree, such as by using pole cores of slightly different diameter, length, or permeability, or by winding two identical pole cores with secondary coils of different numbers of turns. When detected, the resultant composite or difference of the voltages induced in these secondaries as they approach and pass a crack or fissure in a test hole wall undergoes first an excursion of one polarity followed directly by an excursion of opposite polarity, with the median point of the reversal occurring at the instant the gap between secondary pole faces passes the effective midplane of the crack or fissure. Electrical differentiation of such detected composite signal produces a single monopolarity impulse at the described instant and of a magnitude proportional generally to probe speed and the size or eddy current disruptive effect of the crack or other wall defect encountered. Display of such differentiation impulse on a sweep trace of the cathode ray tube screen provides a uniquely definitive indication of magnitude and location of the defect.

A further feature resides in the hand-held test probe head on a side of which addressed to the operator is an alert lamp or other prominently visible display. Circuit means responsive to the amplitude of the monopolarity differentiated pulse signals, preset to reject those below a certain level, operates the lamp and for stronger signals thereby alerts the operator when a defect is encountered. Thereupon the operator's attention may then be turned to the cathode ray tube screen for a more detailed evaluation of the signal information.

Still other features reside in the circuit means for operating the cathode ray tube indicator by sweep traces maintained at constant amplitude substantially independently of battery voltage changes or probe speed variations. A permanent magnet mounted on the rotary probe cooperates with a stationary induction coil that produces an impulse each time the magnet traverses the face of the coil. The magnitude of the pulse is directly proportional to probe speed of rotation, whereas the timing of the impulse always corresponds to a given position of the probe during each rotation. Such impulse applied to a peak detector circuit produces a charge voltage proportional to probe speed, which voltage is also applied as a CRT sweep synchronizing signal to a solid state switch connected across the capacitor of the RC integrating circuit. The switch is momentarily closed by this signal so as to instantly discharge the capacitor to a predetermined reference level and immediately thereupon release the same to start the integration function of the capacitor. This provides the desired recurring CRT sweep function. With such an arrangement any tendency for rotary probe speed to increase or decrease is accompanied by proportionately increased or decreased induced impulse voltage, and thereby increased or decreased charging voltage applied to the RC integrating circuit. Simultaneously therewith an offsetting decrease or increase, respectively, in the charging time or duration of the charging cycle occurs. As a result, the sawtooth sweep voltage applied to the sweep electrodes of the cathode ray tube undergoes the same linear voltage excursion on successive sweeps, although at sweep rates subject to variation, regardless of rotor speed. Furthermore, since these mutually offsetting variables are developed independently of battery voltage variation in the system, the signal display is virtually independent of such voltage variations.

These and other features, objects and advantages of the invention, will become more fully evident as the description proceeds by reference to the accompanying drawings.

DETAILED DESCRIPTION OF THE PREFERRED EMBODIMENT

Figure 1:
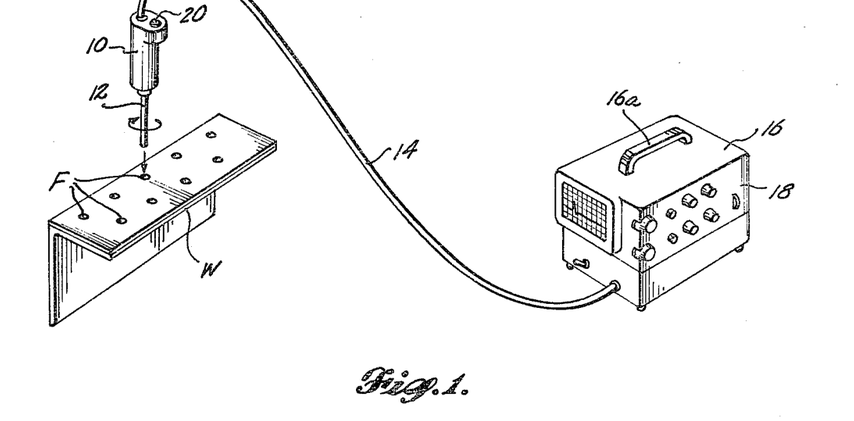
FIG. 1 is a perspective view of the improved portable fault detection apparatus positioned for testing fastener holes in a workpiece also shown in the drawings.

Referring to the drawings, the improved fault detector apparatus, including the hand-held test head 10 that mounts the rotary eddy current probe 12, is electrically connected by a flexible multiconductor cord 14 to the cathode ray tube oscilloscope module 16 that is preferably coupled with the power pack and electronic circuitry module 18. The combined modules are conveniently manufactured in a highly compact form suitable for hand carrying by means of handle 16a. The entire apparatus can readily be manufactured to weigh less than ten pounds with the hand-held test head 10 less than one-tenth of the total weight and of a configuration that can be held and efficiently manipulated over long periods of time without tiring the operator.

As depicted in FIG. 1, the test head 10 with rotary probe 12 is shown poised in position for use in conjunction with the work W having a plurality of fastener holes F to be tested for fissures, cracks or other flaws. This testing is accomplished by inserting the rotary test probe 12 into each hole and advancing the same to increasing depths so as to rotatively scan the juxtaposed regions of the wall of the hole. Rotation of the eddy current probe 12 at a speed of the order of 3,000 revolutions per minute causes the sensing transformer elements to rotatably scan the periphery of the hole wall and produce fault detection signals capable of indication on the cathode ray tube screen and also on the test head by way of the alert indicator light 20. The latter is preferably mounted on the top side of the hand-held test head where it will be prominently visible by the operator conducting the tests. In the course of conducting a series of tests, all the operator need do in addition to properly manipulating the probe in the test holes one by one, is to observe the alert lamp 20 until such time as an alert signal is indicated revealing the presence of a fault or aberration in a test hole requiring closer scrutiny. At that point, the operator continues to maintain the rotating test probe in the test hole and turns his attention to the screen of the cathode ray tube indicator 16 so as to observe the electron beam trace on the screen. The indicator unit and associated circuitry is so designed as to display a fault signal on the tube representative of both the magnitude of the fault and also the position of the fault about the periphery of the test hole. Depending upon the indication, the operator is either able to reject the workpiece or approve it for use. Throughout this procedure it will be observed that the operator's energies and abilities to concentrate on those cases where careful study of signals are necessary are conserved because for all other cases it is merely necessary to maintain a watch for operation of the alert lamp, a much less exacting and less demanding procedure.

Figure 2:
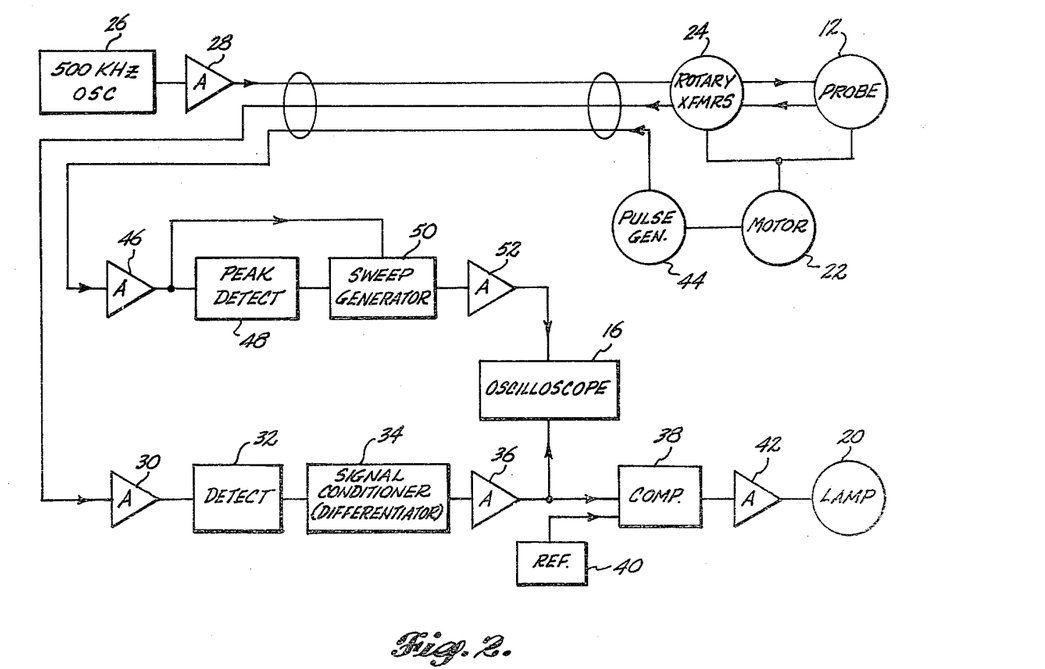
FIG. 2 is a block diagram of the apparatus.

In brief general terms with reference to FIG. 2, probe 12 is rotatively driven by a battery operated DC motor 22. The probe incorporates eddy current sensing elements to be described that include three electrical windings to and from which electrical coupling is established by way of rotary transformers 24 that avoid the necessity for electrical slip rings and the like that could induce noise or false signal effects in the output leads of the eddy current sensing coils. The eddy current response effects or signals from the sensing coils are very small in magnitude, and inasmuch as the use of slip rings or other mechanical contact couplings to transfer those signals from the rotary probe to the response circuits could also introduce cyclic effects phase related to the repeating rotational positions of the rotary probe, it is best to use rotary transformers which avoid all physical contacts for electrical coupling.

As will later appear, a high-frequency alternating voltage from a source 26, such as a 500 kilohertz oscillator, raised to suitable amplitude level by an amplifier 28, is coupled through a rotary transformer 24 to the primary winding of the probe eddy current sensing unit.

High-frequency voltage induced in the secondaries of the probe sensing unit that are modified by the presence of a fault in the wall of a test hole during probe rotation are transmitted through a rotary transformer 24 to signal amplifier 30, rectified in a detector 32 and processed in a signal conditioner or differentiator circuit 34. The output of the differentiator circuit 34 is raised to appropriate amplitude level by an amplifier 36 for application both to the signal deflection elements of an oscilloscope indicator 16 and to one input of a comparator circuit 38. The other input of such comparator circuit 38 comprises a voltage reference source 40 with which the amplitude or magnitude of the signal from amplifier 36 is compared. In conventional manner, the comparator circuit 38 is designed and adjusted such that if the signal from amplifier 36 exceeds the reference level, the comparator produces an output that is amplified in circuit 42 and applied to energize the indicator lamp 20. If the signal from a fault or other condition in the test hole causing variation in the eddy current pickup coils is below a certain amplitude, however, the lamp 20 will not be energized during testing of hole. Adjustment of the value of the reference voltage level from reference source 40 permits the operator to select that threshold value of signal amplitude from amplifier 36 at which the lamp will be energized.

The disclosed system also includes as an important feature of the invention, a special sweep circuit for operating the oscilloscope 16. While later described in greater detail, this sweep arrangement includes a pulse generator means 44 operable cyclically with probe rotation to produce an impulse for application to amplifier 46 at a certain point in each cycle of probe rotation. Moreover, the impulse produced by the generator 44 has an amplitude that is proportional to rotational velocity of the probe. The amplified impulse from amplifier 46 is applied both to a peak detector 48 and to a sweep generator 50 to produce recurring linear sawtooth waves. These are amplified to appropriate level in amplifier 52 and applied to the sweep deflection elements of the oscilloscope 16 in conventional manner. The important function of the sweep circuit disclosed is to not only generate oscilloscope sweep voltages that are precisely synchronized and phase related to probe rotation, but that remain of constant amplitude despite variation in speed of probe rotation, and without regard to changes in battery source voltage operating the system as a whole. In this latter regard, having reference to the initially stated objectives of the invention, it will be appreciated that the amplifier circuits 46 and 52, as well as the internal circuits of the oscilloscope 16, are suitably designed using known techniques to provide fixed amplification independently of battery source voltage changes, leaving the problem of generating constant-amplitude sweeps for the oscilloscope to other provisions in the sweep generating circuits to be described hereafter in greater detail.

Figures 3, 4:
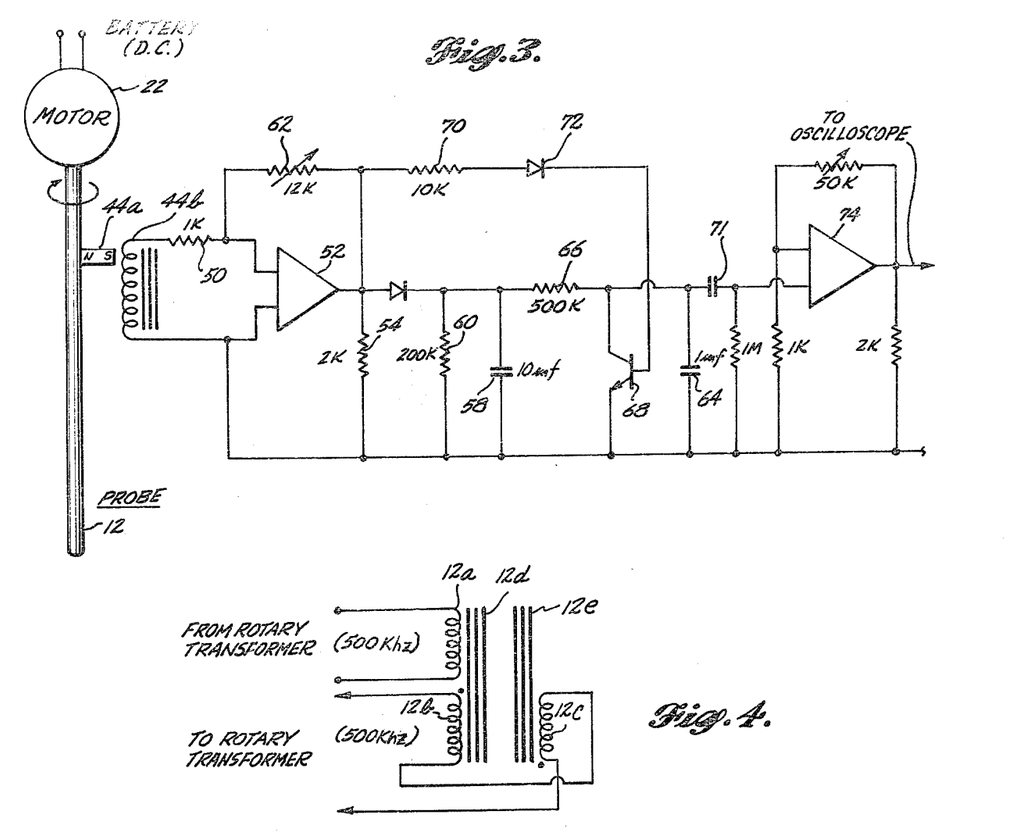
FIG. 3 is a schematic of the cathode ray tube sweep generating portion of the system.
FIG. 4 is an electrical diagram showing the primary and associated differentially connected secondary coils.

As depicted in FIG. 3, the pulse generator means 44 comprises a permanent magnet 44a mounted on the shaft of motor 22 (i.e., fixed to rotate with the probe 12) in a position to sweep past a complemental induction coil 44b mounted in the test head 10 at a fixed position adjacent the path of rotation of the permanent magnet. The induction coil 44b being stationarily mounted in fixed relation to the test unit 10, an impulse is generated in the induction coil by the magnet with each such traversal as the probe 12 reaches a certain rotational position. That position can be regarded as the zero position or initiation point for each sweep or scan of the test hole by rotation of the probe. With the probe rotating at approximately 3,000 revolutions per minute, short voltage impulses will appear across the terminals of the induction coil 44b at a corresponding frequency, which frequency will increase or decrease with changes of probe rotation speed. Moreover, the amplitude of the induced impulses in induction coil 44b will also increase or decrease with increase and decrease of probe rotation speed due, of course, to the fact that the rate at which lines of force from the magnet cut the turns of the induction coil determines the induced voltage.

The induced voltage impulses from induction coil 44b are applied through resistor 50 to the input of amplifier 52 and at amplified level are impressed on a peak detector circuit including an input resistance 54, a diode rectifier 56, a storage condenser 58, and a discharge resistor 60 connected across the storage condenser. Operational characteristics are imparted to the amplifier 52 by an adjustable feedback resistor 62. With this circuit arrangement the charge voltage stored on storage condenser 58 is proportional to the peak amplitude of the synchronizing impulses appearing across the terminals of induction coil 44b. Should those impulses increase or decrease in amplitude, the charge voltage carried by storage condenser 58 will closely follow and remain proportional to those changes. There will be a slight lag, of course, because of the time constant of the peak detection circuit, but this lag can be kept sufficiently low for condenser charge voltage to closely track the impulse amplitude changes and thereby to remain closely and currently proportional to variations in rotational speed of probe 12. The voltage thus maintained by the storage condenser 58 is applied to an RC integrating circuit, including a sweep condenser 64 and a charging resistance 66. A transistor switch 68 is connected directly across the sweep condenser 64, with the base electrode of the transistor connected to receive the amplified impulses from amplifier 52 through a resistance 70 and series diode 72. The design is such that with each impulse delivered by the induction coil 44b, a brief switching voltage is applied between the base and the emitter of transistor 68 to momentarily render the transistor highly conductive, that is, to act as a closed switch connected across the sweep condenser 64. During this brief switch closure period, condenser 64 instantly discharges through the switch. Upon termination of the impulse applied to the transistor base, sweep condenser 64 starts charging at a linear rate through the resistance 66 from the voltage applied by storage condenser 58. The process is repeated with inception of each succeeding impulse induced in coil 44b. As a result, successive sawtooth sweep voltages are developed in the integrating circuit across the terminals of sweep condenser 64. These vary in frequency with frequency variations of the impulses from coil 44b, hence with variations in shaft speed. However, although such variations represent variation in the charging period of capacitor 64, these do not change the magnitude of the sawtooth sweep wave, nor thereby the linear sweep length of the electron beam traversing the face of the cathode ray tube oscilloscope. This is true because the amplitude of induced impulses in induction coil 44b also changes with variations in probe speed and these are reflected in corresponding changes in the voltage stored on storage condenser 58. Consequently, although the interval between successive switching impulses applied to transistor 68 changes with probe speed, so will the charging voltage applied to the integrating circuit and in a manner to compensate. The broad concept of providing compensation for changes in charging interval so as to generate constant amplitude sweep voltages for cathode ray tube displays is not new in the art, as indicated by the above-cited references; however, the unique, simplified manner in which the present invention achieves this for the fulfillment of related objectives of the invention is considered to represent a significant contribution to the art.

The recurring sawtooth wave generated by the sweep circuit and appearing across sweep condenser 64 is coupled through capacitor 71 to the input of an amplifier 74 of suitable design for application to the sweep deflection elements of the cathode ray oscilloscope 16 as shown.

Figure 5:
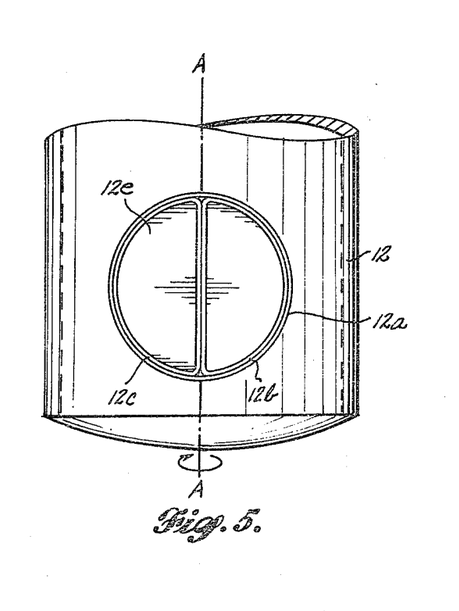
FIG. 5 is an enlarged side detail view of the probe tip showing the transformer sensing coils and associated pole cores viewed endwise.
Figure 9:
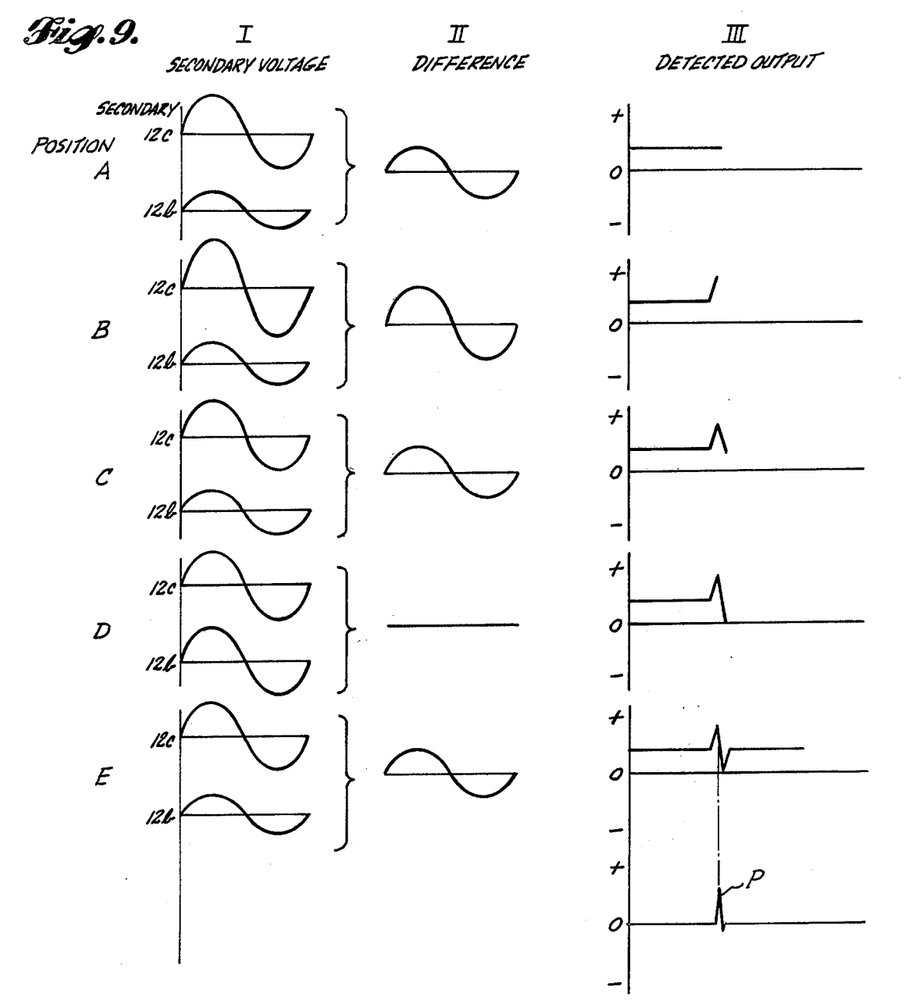
FIG. 9 is a wave diagram showing probe transformer primary and secondary coil excitation voltages and, on a different time scale, associated detected and differentiated response signals.

As has already been mentioned in conjunction with FIG. 2, the indicator system of the invention incorporates a signal conditioner or differentiator 34 that produces a unique and informative signal for application to the oscilloscope signal deflection electrodes with each rotation of the probe carrying its eddy current fault sensing elements past the location of a fissure, crack or other fault in the wall of the test hole. In the past, with balanced sensing secondary pole cores performing the sensing function, the high frequency voltages induced in the transformer secondaries differentially connected in the input of the signal detection circuit constituted two closely spaced impulses of the same polarity and of equal amplitudes. To the unschooled or inattentive operator, these two impulses could conceivably be construed as if they represented two distinct faults in the wall of the test hole, or perhaps as the leading and lagging edge regions of a single wide fault which, of course, would not be true. As a further feature of the invention therefore, the two sensing secondaries of the eddy current probe, as shown in FIGS. 4 to 8, are given a predetermined slight degree of mismatch with the consequent effect on output response of the composite signals delivered by the differentially connected secondaries as depicted in FIG. 9. In the preferred construction of the eddy current sensing elements of the rotary probe, there is a single primary winding 12a and two secondary windings 12b and 12c. The respective secondary windings are each wrapped as a layer of turns of very fine copper wire on the respective elongated pole core pieces 12d and 12e. These ferrite pole cores are semicircular in cross section with their flat sides positioned adjacent each other and separated by a very thin air gap that is essentially filled by the thickness of the secondary windings surrounding each as shown in FIG. 5. The primary winding 12a surrounds the assembly and therefore is commonly coupled to both coils and both pole cores.

The desired mismatch of eddy current induction sensitivity of the two secondaries may be accomplished by using a different number of turns on the two secondaries, by a built-in difference in the cross sectional areas of the respective secondary pole cores, or by slight differences in the lengths of these pole cores or in the extent they project in relation to the peripheral face of the probe. In any event, the difference is manifested as an induced voltage difference as reflected in FIG. 9, diagram I for probe rotary position A. In that illustration, it will be seen that the high-frequency voltage induced in secondary 12c is of greater amplitude than that induced in 12b with the probe in position A, assumed to be a position in which the pole core faces both confront a non-faulty test hole wall area. The difference voltage of the differentially connected secondary windings 12b and 12c appears in graph II for probe rotary position A, and the detected output or DC level representing that AC difference voltage appears as a given DC level in graph III.

Figure 6:
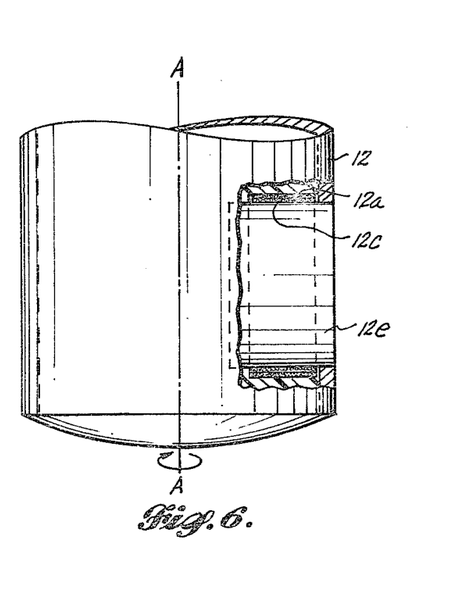
FIG. 6 is a side view of the same taken at right angles to the view in FIG. 5.

Noting that the two secondary core poles are positioned in a common plane of rotation of the probe perpendicular to the rotational axis A—A shown in FIGS. 5 and 6, when as in rotary position B these rotating elements first encounter a crack or fissure in the wall of the test hole in the arrangement shown in FIGS. 5 and 6, the secondary winding 12c (shown as leading) is influenced by the encounter before the winding 12. Thus, the eddy current loading of secondary 12c drops abruptly and the amplitude of induced voltage in secondary 12c correspondingly rises. The initial difference between amplitudes of induced voltage in the two secondaries therefore also rises, producing the increased detected output as depicted in graphs II and III, respectively. As the probe rotates a small amount past position B, the induced voltage in secondary 12c abruptly decreases. It reaches its initial differential relationship with that in 12b at the point when the midplane between the two secondary core poles 12d and 12e and the effective center of the wall crack coincide. This is as depicted in the position C in FIG. 9. Thereupon continued rotation of the probe in the same direction causes the effect of the crack to predominantly affect the secondary 12b. With the probe in position D the difference between the two secondary induced voltages has become zero as depicted, whereas further advance to position E restores the initial or residual difference of induced voltages between the two differentially connected secondaries. By this point the wall crack is passed, the two secondaries are again addressed only to non-faulty wall material in the test hole and a steady DC level is produced in the output of the signal differentiator 34.

Figure 7:
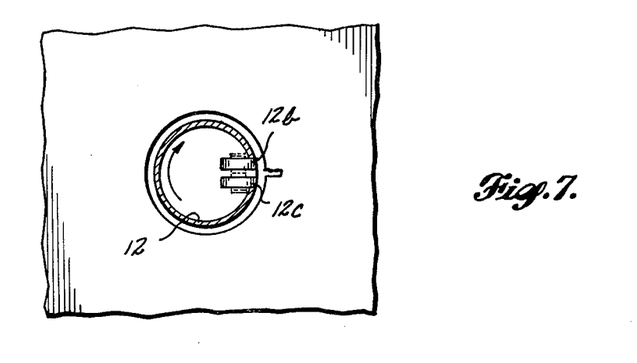
FIG. 7 is a simplified probe end view showing the sensing coil elements.
Figure 8:
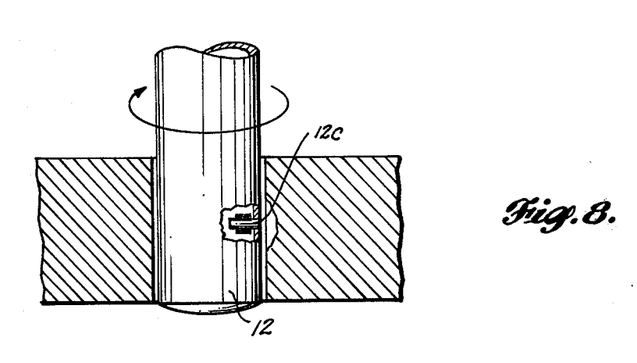
FIG. 8 is a simplified side view of the probe tip in a test hole.

As shown in the detected voltage graph in column III beneath the composite response curve depicted in position E, the composite response has been differentiated in circuit 34 to produce a monopolar pulse P. The peak of this pulse will be seen to coincide with the midposition of the transition between positive and negative excursions of the detected composite output from the two secondary coils. Thus, the detected differentiated or processed output signal from the differentially connected coils represents a singular unique pulse depicting, by its magnitude, the extent or degree of fault in the test hole wall, whereas the timing position of this pulse, such as the point where it apears on the linear sweep display of the CRT indicator coincides exactly with the point at which the midplane between the two pole core test elements registers with the effective center of the wall crack (FIG. 7).

In the operation of the instrument described the probe is rotated at relatively high speed as indicated, such as between 2,000 and 4,000 revolutions per minute, in order that the entire surface of the fastener hole wall (or walls if there are two or more parts laminated together) may be scanned progressively to different depths by the rotating eddy current sensing transformer poles in a relatively short time period. Observance of alert indicator lamp 20 on the hand-held test head alerts the operator when a fault is detected. At that point the operator turns attention to the cathode ray tube screen for detailed analysis of the fault signal magnitude and position there indicated. This enables the operator to distinguish between cracks, gouges and out-of-round conditions, any of which might operate the fault indicator 20.

These and other advantages of the invention will be evident to those skilled in the art based on an understanding of the foregoing disclosure of the presently preferred embodiment. It will be appreciated by those persons that a number of variations in design are readily possible and that the particular packaging and configuration of the instrument as well as the circuit details and design details of the eddy current test probe itself are also subject to some variation within the realm of ordinary skill. Accordingly, it is the intent to define the invention including the features and combinations of features thereof in the claims that follow and thereby to cover equivalents as well.

The embodiments of the invention in which an exclusive property or privilege is claimed are defined as follows:

1. Portable eddy current rotary probe type test apparatus for detecting faults in the walls of test holes and the like comprising a test head, including a rotary test probe projecting therefrom and means to rotatively drive said probe, said probe having an end portion insertable in a test hole which end portion includes a transformer primary and two transformer secondaries, including parallel secondary ferromagnetic core elements arranged in a common plane of rotation of the probe and having pole ends facing radially outwardly from the periphery of said probe, said secondaries having a predetermined slight degree of mismatch whereby, with the probe rotating in a test hole and the primary energized by high frequency current, voltages are induced in said secondaries influenced by eddy currents in the hole wall that change by respectively different amounts as such secondaries successively encounter a fault in such wall during each probe rotation cycle, circuit means connecting said secondaries differentially and detecting the composite signal therefrom to produce successive voltage excursions in response to a fault respectively above and below that from the secondaries while they are traversing nonfaulty hole wall regions, means to differentiate said detected composite fault signal so as to produce a monopolarity pulse therefrom at the transition between said excursions, and indicator means responsive to such monopolarity pulse.

2. The apparatus defined in claim 1, including a test head that is adapted to be hand-held operatively for insertion and removal of the test probe into and from a test hole, a prominently visible indicator element on said test head in a position to be readily observed by a person operatively holding the test head, level comparator means responsive to said detected composite signal and operable to compare the level thereof produced by a hole fault with a predetermined reference value, thereby to operate said visible indicator when said signal exceeds said predetermined reference value.

3. The apparatus defined in claim 2, further including a cathode ray tube oscilloscope indicator physically separate from but electrically connected to said test head and including sets of electron beam deflection elements respectively operable to sweep the cathode ray tube beam in a predetermined path cyclically in response to recurring sweep signals and to deflect the beam transversely thereto during said sweeps in response to applied fault indicating signals, respectively, sweep means for said cathode ray tube oscilloscope including cooperating permanent magnet and induction coil elements, one of such latter elements being mounted to rotate with said rotary probe and the other of such latter elements being stationarily mounted in said test head to induce in such coil element at a predetermined rotary position of the probe a voltage pulse that varies in amplitude and recurrence frequency with probe rotational velocity, charging circuit means including a storage capacitor and means responsive to said induced pulses from said coil element to maintain a charge voltage on said storage capacitor that varies with the amplitude of said induced pulses, and RC integrating circuit means including a sweep capacitor connected to said cathode ray tube oscilloscope electron beam sweep deflection elements and connected to said storage capacitor through a charging resistor, and switch means operatively connected across said sweep capacitor including a control element connected to said induction coil element operable to close said switch means and thereby instantly discharge said sweep capacitor with each pulse from said induction coil element, and means connecting said cathode ray tube oscilloscope electron beam signal deflection elements to said differentiating means to display said monopolarity pulses on said oscilloscope.

4. The apparatus defined in claim 1, further including a cathode ray tube oscilloscope indicator physically separate from but electrically connected to said test head and including sets of electron beam deflection elements respectively operable to sweep the cathode ray tube beam in a predetermined path cyclically in response to recurring sweep signals and to deflect the beam transversely thereto during said sweeps in response to applied fault indicating signals, respectively, sweep means for said cathode ray tube oscilloscope including cooperating permanent magnet and induction coil elements, one of such latter elements being mounted to rotate with said rotary probe and the other of such latter elements being stationarily mounted in said test head to induce in such coil element at a predetermined rotary position of the probe a voltage pulse that varies in amplitude and recurrence frequency with probe rotational velocity, charging circuit means including a storage capacitor and means responsive to said induced pulses from said coil element to maintain a charge voltage on said storage capacitor that varies with amplitude of said induced pulses, and RC integrating circuit means including a sweep capacitor connected to said cathode ray tube oscilloscope electron beam sweep deflection elements and connected to said storage capacitor through a charging resistor, and switch means operatively connected across said sweep capacitor including a control element connected to said induction coil element operable to close said switch means and thereby instantly discharge said sweep capacitor with each pulse from said induction coil element, and means connecting said cathode ray tube oscilloscope electron beam signal deflection elements to said differentiating circuit means to display said monopolarity pulses on said oscilloscope.

5. Portable eddy current rotary probe type test apparatus for detecting faults in the walls of test holes and the like comprising a test head, including a rotary test probe projecting therefrom and means to rotatively drive said probe, said probe having an end portion insertable in a test hole, which end portion includes a transformer primary and two transformer secondaries, including parallel secondary ferromagnetic core elements arranged in a common plane of rotation of the probe and having pole ends facing outwardly from the periphery of said probe whereby, with the probe rotating in a test hole and the primary energized by high-frequency current, voltages are induced in said secondaries influenced by eddy currents in the hole wall that change as such secondaries successively encounter a fault in such wall during each probe rotation cycle, circuit means connecting said secondaries differentially and detecting the composite signal therefrom to produce successive voltage excursions in response to a fault, and indicator means including a cathode ray tube oscilloscope indicator physically separate from but electrically connected to said test head and including sets of electron beam deflection elements respectively operable to sweep the cathode ray tube beam in a predetermined path cyclically in response to sweep signals and to deflect the beam transversely thereto during said sweeps in response to applied deflection signals, respectively, sweep means for said cathode ray tube oscilloscope including cooperating permanent magnet and induction coil elements, one of such latter elements being mounted to rotate with said rotary probe and the other of such latter elements being stationarily mounted in said test head to induce in such coil element at a predetermined rotary position of the probe a voltage pulse that varies in amplitude and recurrence frequency with probe rotational velocity, charging circuit means including a storage capacitor and means responsive to said induced pulses from said coil element to maintain a charge voltage on said storage capacitor that varies with amplitude of said induced pulses, and RC integrating circuit means including a sweep capacitor connected to said cathode ray tube oscilloscope electron beam sweep deflection elements and connected to said storage capacitor through a charging resistor, and switch means operatively connected across said sweep capacitor including a control element connected to said induction coil element operable to close said switch means and thereby instantly discharge said sweep capacitor with each pulse from said induction coil element, and means connecting said cathode ray tube oscilloscope electron beam signal deflection elements to said circuit means to display said composite signal on said oscilloscope.

6. The apparatus defined in claim 5, including a test head that is adapted to be hand-held operatively for insertion and removal of the test probe into and from a test hole, a prominently visible indicator element on said test head in a position to be readily observed by a person operatively holding the test head, level comparator means responsive to said detected composite signal and operable to compare the level thereof produced by a hole fault with a predetermined reference value, thereby to operate said visible indicator when said signal exceeds said predetermined reference value.

* * * * *